US012514697B2

(12) United States Patent
Katayama et al.

(10) Patent No.: US 12,514,697 B2

(45) Date of Patent: Jan. 6, 2026

(54) CHOLECYSTITIS TREATMENT VIA GALLBLADDER-DUODENUM FISTULA

(71) Applicant: OLYMPUS MEDICAL SYSTEMS CORP., Tokyo (JP)

(72) Inventors: Tomofumi Katayama, Kunitachi (JP); Tomohiko Mamiya, Kawasaki (JP); Mitsuki Sato, Hino (JP); Keita Shoji, Fuchu (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 398 days.

(21) Appl. No.: 18/170,067

(22) Filed: Feb. 16, 2023

(65) Prior Publication Data

US 2023/0263616 A1 Aug. 24, 2023

Related U.S. Application Data

(60) Provisional application No. 63/362,819, filed on Apr. 11, 2022, provisional application No. 63/268,260, filed on Feb. 18, 2022.

(51) Int. Cl.

| | |
|---|---|
| ***A61F 2/04*** | (2013.01) |
| ***A61B 17/11*** | (2006.01) |
| ***A61M 27/00*** | (2006.01) |

(52) U.S. Cl.

CPC ............ *A61F 2/04* (2013.01); *A61B 17/1114* (2013.01); *A61M 27/002* (2013.01); *A61B 2017/1139* (2013.01); *A61F 2002/041* (2013.01)

(58) Field of Classification Search

CPC .. A61F 2/04; A61F 2002/041; A61B 17/1114; A61B 2017/1139; A61B 2017/00818; A61M 27/002

See application file for complete search history.

(56) References Cited

U.S. PATENT DOCUMENTS

| | | | | |
|---|---|---|---|---|
| 8,460,314 | B2 | 6/2013 | Kaji et al. | |
| 9,486,219 | B2 * | 11/2016 | Van Dam | A61M 27/008 |
| 2005/0273033 | A1 * | 12/2005 | Grahn | A61M 27/002 604/9 |

(Continued)

FOREIGN PATENT DOCUMENTS

| | | | | |
|---|---|---|---|---|
| JP | 2019098111 | A | 6/2019 | |
| KR | 20160121146 | A * | 10/2016 | |
| WO | WO-2008027720 | A2 * | 3/2008 | A61F 2/04 |

OTHER PUBLICATIONS

Science Direct: Cystic Duct (https://www.sciencedirect.com/topics/immunology-and-microbiology/cystic-duct#related-terms, accessed May 14, 2025, showing information published in 2018 from Principles of Gynecologic Oncology Surgery by Chiva et al.). (Year: 2025).*

(Continued)

*Primary Examiner* — Ariana Zimbouski

(74) *Attorney, Agent, or Firm* — Schwegman Lundberg & Woessner, P.A.

(57) ABSTRACT

According to an aspect, a method of cholecystitis treatment includes: forming a communication hole that communicates a gallbladder and a duodenum; and arranging a bypass tube extending from a cystic duct to the duodenum through an inside of the gallbladder and the communication hole.

16 Claims, 9 Drawing Sheets

(56) References Cited

U.S. PATENT DOCUMENTS

| | | | | |
|---|---|---|---|---|
| 2015/0313598 | A1* | 11/2015 | Todd | A61B 17/1114 606/153 |
| 2017/0007276 | A1* | 1/2017 | Pradhan | A61B 17/1114 |
| 2017/0072173 | A1* | 3/2017 | Van Dam | A61B 17/1114 |
| 2017/0165458 | A1* | 6/2017 | Yu | A61M 27/002 |
| 2018/0078745 | A1* | 3/2018 | Gray | A61B 17/1114 |
| 2018/0280669 | A1* | 10/2018 | Shlomovitz | A61M 27/002 |

OTHER PUBLICATIONS

In brief: How does the gallbladder work (https://www.ncbi.nlm.nih.gov/books/NBK279386/#:~:text=Last%20Update%3A%20April%2027%2C%202021,concentrates%20bile%20from%20the%20liver., accessed May 14, 2025 and last updated Apr. 27, 2021). (Year : 2021).*

* cited by examiner

CHOLECYSTITIS TREATMENT VIA GALLBLADDER-DUODENUM FISTULA

RELATED APPLICATION DATA

This application is based on and claims priority under 37 U.S.C. § 119 to U.S. Provisional Application No. 63/268,260 filed on Feb. 18, 2022, and No. 63/362,819 filed on Apr. 11, 2022, the entire contents of which are incorporated herein by reference.

FIELD OF DISCLOSURE

This document relates to systems, devices, and methods of cholecystitis treatment.

BACKGROUND

In the bile duct system, which is a luminal organ, the gallbladder exists as a sac-like part, which is ordinarily connected via a cystic duct to an "upstream" common hepatic duct receiving bile from a liver also to a "downstream" common bile duct, which carries bile to the intestine.

Acute cholecystitis, which is one of the diseases of the gallbladder, often occurs when calculus generated in the gallbladder moves to a cystic duct.

A current standard treatment for acute cholecystitis is laparoscopic cholecystectomy, which invasively removes the gallbladder. In laparoscopic cholecystectomy, there is no risk of recurrence because the gallbladder is removed, but there is room for improvement in terms of invasiveness to the patient because it is an invasive surgical procedure.

U.S. Pat. No. 8,460,314 describes a method of puncturing the gallbladder from a gastrointestinal tract under ultrasonic endoscopy and eliminating the function of the gallbladder mucosa by cauterization or the like. By eliminating the function of the gallbladder mucosa, bile is not concentrated and formation and growth of calculus are suppressed.

SUMMARY

In the treatment for cholecystitis, this document describes, among other things, systems, devices, and methods for treating cholecystitis. An aspect can include forming a fluid communication hole that communicates a gallbladder and a digestive tract, and arranging a bypass tube extending from a cystic duct to the digestive tract through an inside of the gallbladder and the fluid communication hole. A bypass tube can be arranged, such as including first and second ends and bypass tube body extending therebetween. The bypass tube body defines a fluid communication lumen between the first and second ends for communicating bile fluids therebetween, the first end extends to the cystic duct, the second end extends to a fistula between the gallbladder and a portion of the digestive tract, a length of the bypass tube body is sized to extends from the first end to the second end within the gallbladder of the subject. An anchoring engagement member is located at one or more of the first and second ends of the bypass tube. The bypass tube can help provide a pathway or passage such as a fluid communication lumen between the gallbladder and the duodenum.

DETAILED DESCRIPTION

A method of cholecystitis treatment according to a first embodiment of the present subject matter will be described with reference to FIGS. 1 to 7.

First, the contents of the gallbladder are removed (step A). The contents of the gallbladder are mainly bile and gallstones (calculus). The bile can be removed by gallbladder drainage, and the calculus can be removed using one or more of various treatment tools.

There are basically two access routes to the gallbladder for performing gallbladder drainage, and in this embodiment, any route may be used.

Figure 1:
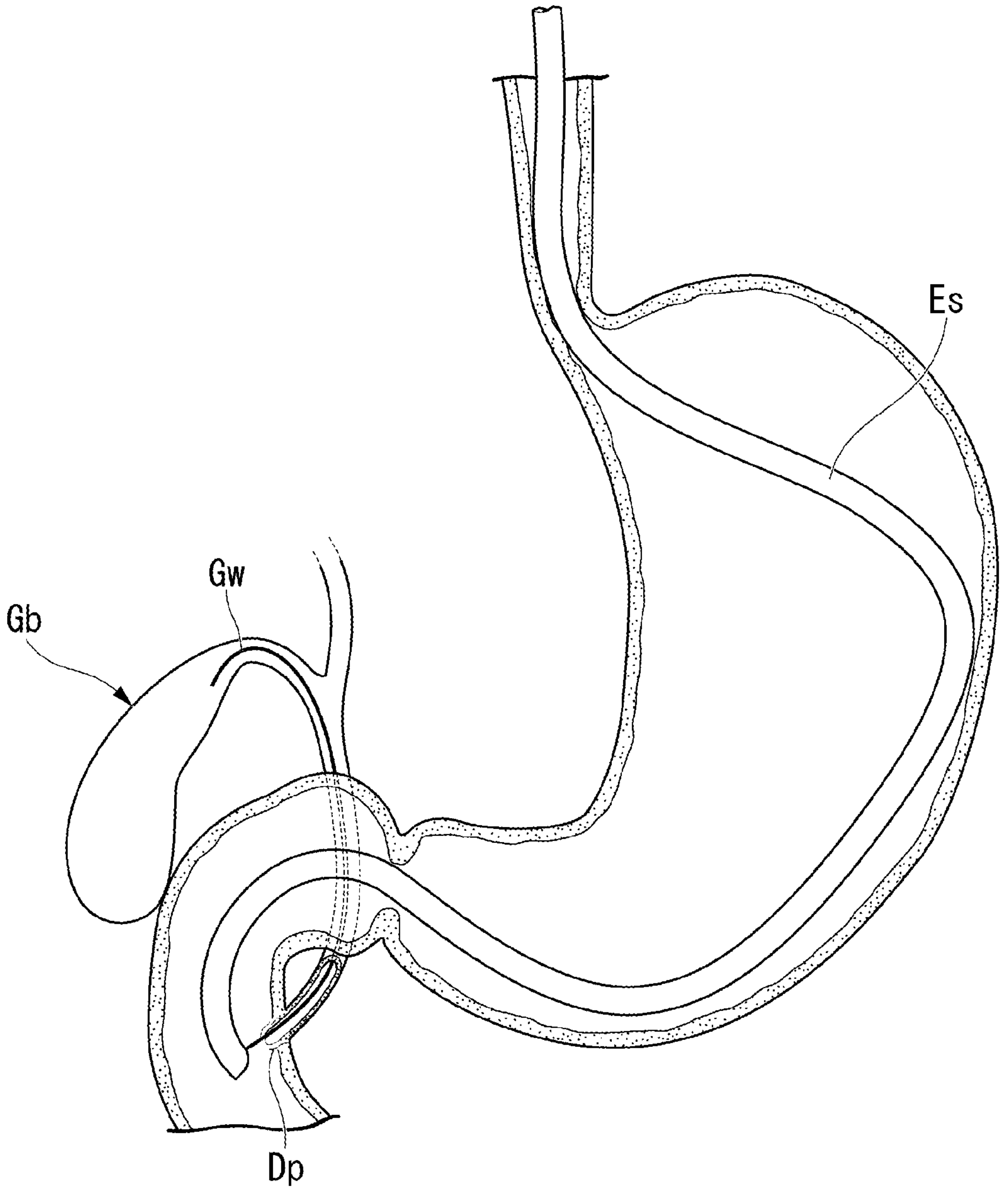
FIG. 1 is a diagram showing an example of an access operation to the gallbladder.

In the transpapillary access route (hereinafter, may be referred to as Route A), as shown in FIG. 1, a guide wire Gw is inserted into the duodenal papilla Dp, such as retrograde from a duodenoscope or another endoscope Es, which is introduced into the duodenum such as by a similar procedure as ERCP (endoscopic retrograde cholangiopancreatography). Then, the distal end of the guide wire Gw is brought into the gallbladder Gb, and the drainage tube is arranged along the guide wire.

In the transperitoneal access route (hereinafter, may be referred to as Route B), while confirming the position of the gallbladder with the image from the ultrasonic endoscope introduced into the duodenum, the puncture needle protruding from the endoscope is inserted into the duodenal wall and then inserted into the gallbladder. Then, with the puncture needle inserted in the gallbladder, the guide wire is passed through the puncture needle, the distal end of the guide wire is made to reach the inside of the gallbladder, and only the puncture needle is removed while leaving the guide wire. Placement of the drainage tube is performed along the placed guide wire. The forming of the communication hole includes puncturing one of (i) the gallbladder Gb from a side of the cystic duct and (ii) the cystic duct from a side of the gallbladder Gb.

Figure 2:
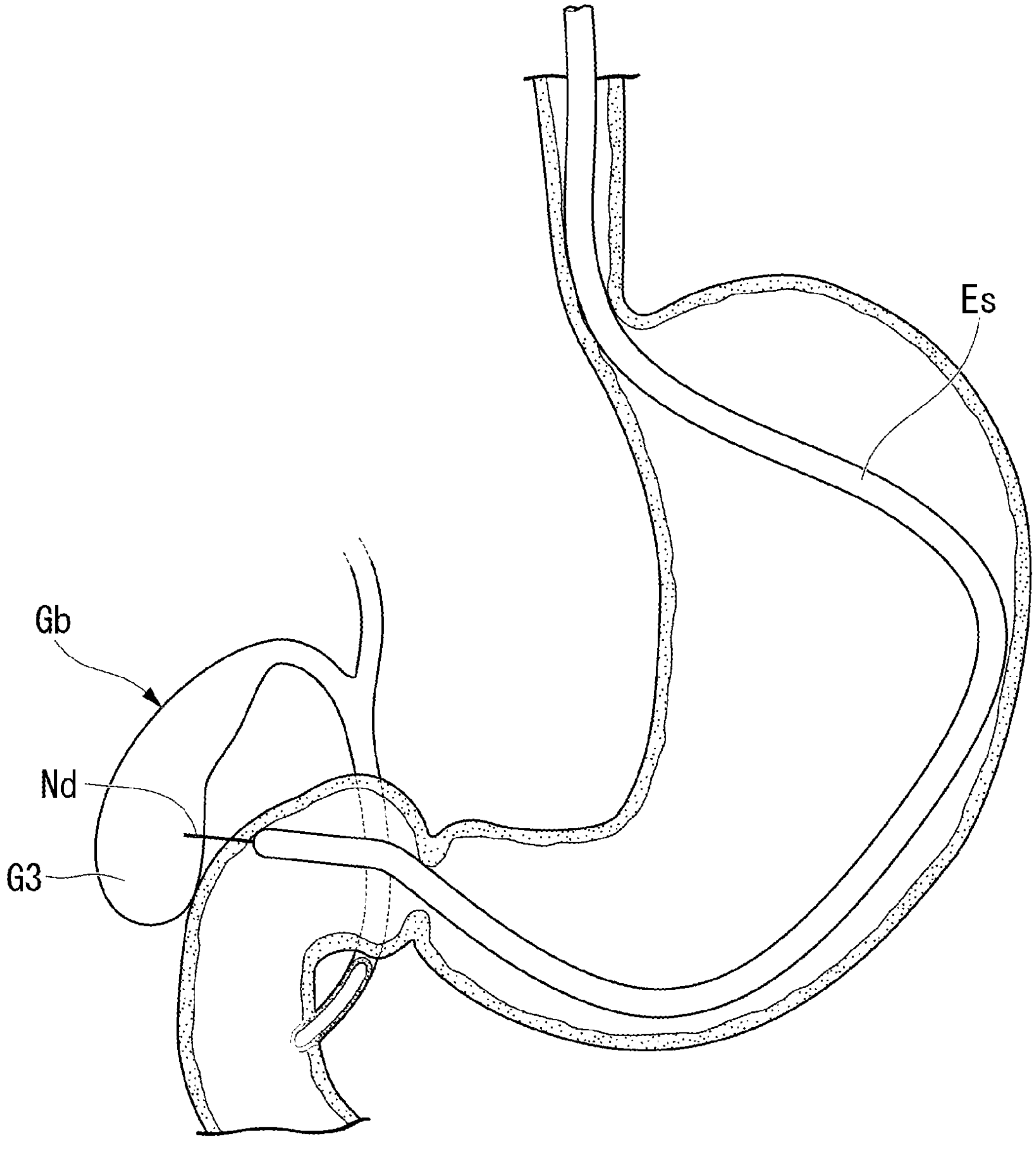
FIG. 2 is a diagram showing an example of an access operation to the gallbladder.

In route B, a drainage route may be established at any of the neck portion, body portion, and bottom portion of the gallbladder, but it may be preferable that a drainage route be established at the bottom portion in consideration of the subsequent procedure described later. When establishing a drainage route at the bottom portion, as shown in FIG. 2, a puncture needle Nd protruding from the endoscope Es is inserted into a bottom portion G3 of the gallbladder Gb. With the puncture needle inserted in the gallbladder, the guide wire is passed through the puncture needle Nd, the distal end of the guide wire is made to reach the inside of the gallbladder, and only the puncture needle is removed while leaving the guide wire. A first hole on a gallbladder and a second hole on a digestive tract are formed.

By the above procedure, a communication hole that communicates the gallbladder and the duodenum is formed. The communication hole that communicates the first hole of the gallbladder and the second hole of the digestive tract may be formed.

Figure 3:
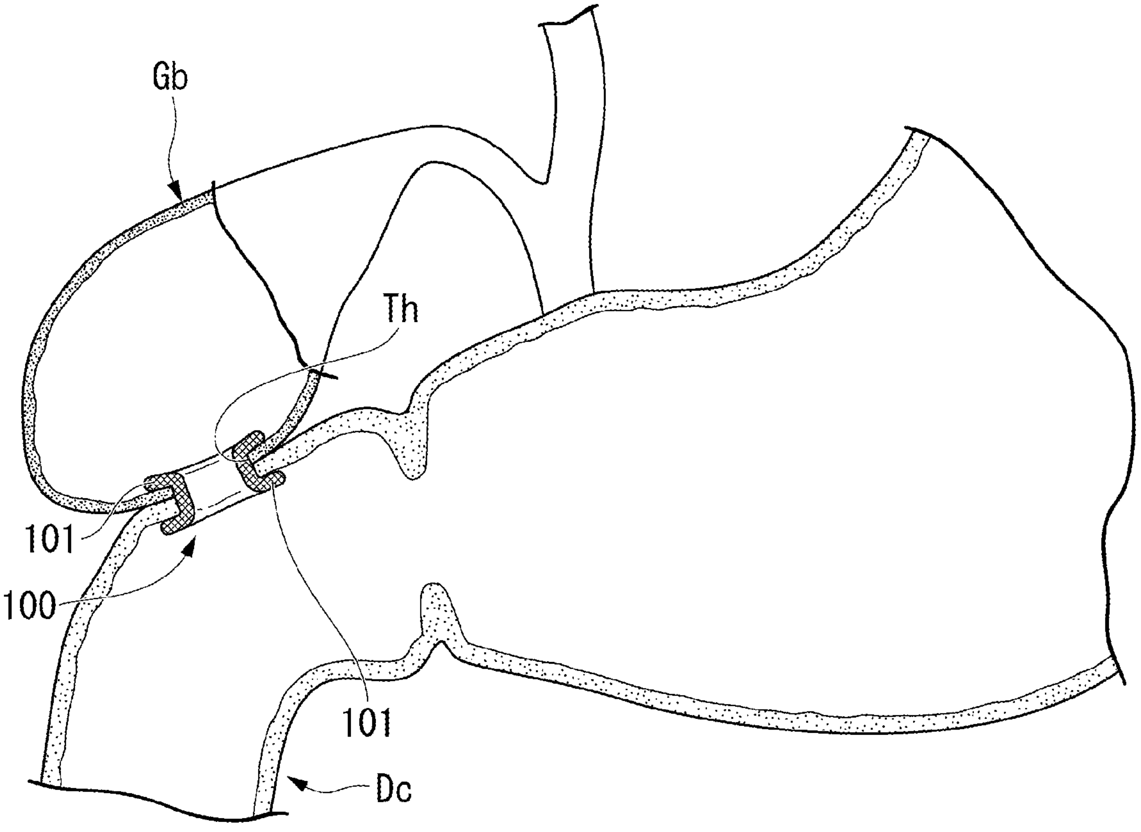
FIG. 3 is an example illustration showing a state in which the gallbladder and the duodenum are placed into fluid communication, such as via a fistula, such as to fluid-communicate with each other by a stent or other port device.

When route B is selected, the distal end of the stent delivery device is made to reach the gallbladder along the placed guide wire, and as shown in FIG. 3, a port device, such as a covered stent connecting the gallbladder and the duodenum can be arranged in a perforation, hole, fistula, or other communication hole Th as a drainage tube, so that the communication hole Th can be stably opened with a sufficient size. The stent is configured to be located at the fistula and to secure the gallbladder to a duodenum, and the stent includes one of (i) flange to secure one or more of a wall of the gallbladder and a wall of the duodenum with respect to the stent, or (ii) suture receptacles for suturing the stent to one or more of a wall of the gallbladder and a wall of the duodenum. The first hole on the gallbladder Gb and the second hole on the digestive tract are formed, the first hole and the second hole are connected to form a connection area. The arranging of the bypass tube 10 includes placing the bypass tube connecting the connection area to the cystic duct. For example, a covered stent 100 shown in FIG. 3 has flanges 101 on both sides of the axial direction of the tubular shape, and is sized, shaped, or otherwise configured such as to capture a corresponding wall portion of the gallbladder Gb such that it is difficult to become detached from the gallbladder Gb and the duodenum Dc after arrangement. A covered stent without a flange 101 can also be used, but in that case it may be preferable to suture the covered stent to the gallbladder or duodenum to help inhibit or prevent it from becoming detached.

If there is calculus in the gallbladder after drainage is completed, the calculus can be removed.

Calculus can be removed by various methods. Specific examples thereof can include removal and crushing with a basket, removal by suction with a suction catheter, and crushing with a laser of a laser irradiation device. The calculus may be removed outside the gallbladder in its original form, or may be removed in a smaller fragment size than the original form such as by crushing or the like.

After removing the contents, the inside of the gallbladder may be washed such as with a physiological saline solution or a drug solution containing an anti-inflammatory agent.

Next, a bypass tube extending from the cystic duct (e.g., engaging, occluding, or sealing the cystic duct) to the outside of the gallbladder or the duodenum through an inside of the gallbladder and the communication hole is installed (step B). The bypass tube may be first arranged in the gallbladder and then arranged in the duodenum by a device that has entered the gallbladder. The bypass tube 10 includes first and second ends and bypass tube body extending therebetween. The bypass tube body define a fluid communication lumen between the first and second ends for communicating bile fluids therebetween. The first end extends to the cystic duct, the second end extends to a fistula between the gallbladder Gb and a portion of the digestive tract. A length of the bypass tube body is sized to extend from the first end to the second end within the gallbladder Gb of the subject. The anchoring engagement member 11 is located at one or more of the first and second ends of the bypass tube 10.

Figure 4:
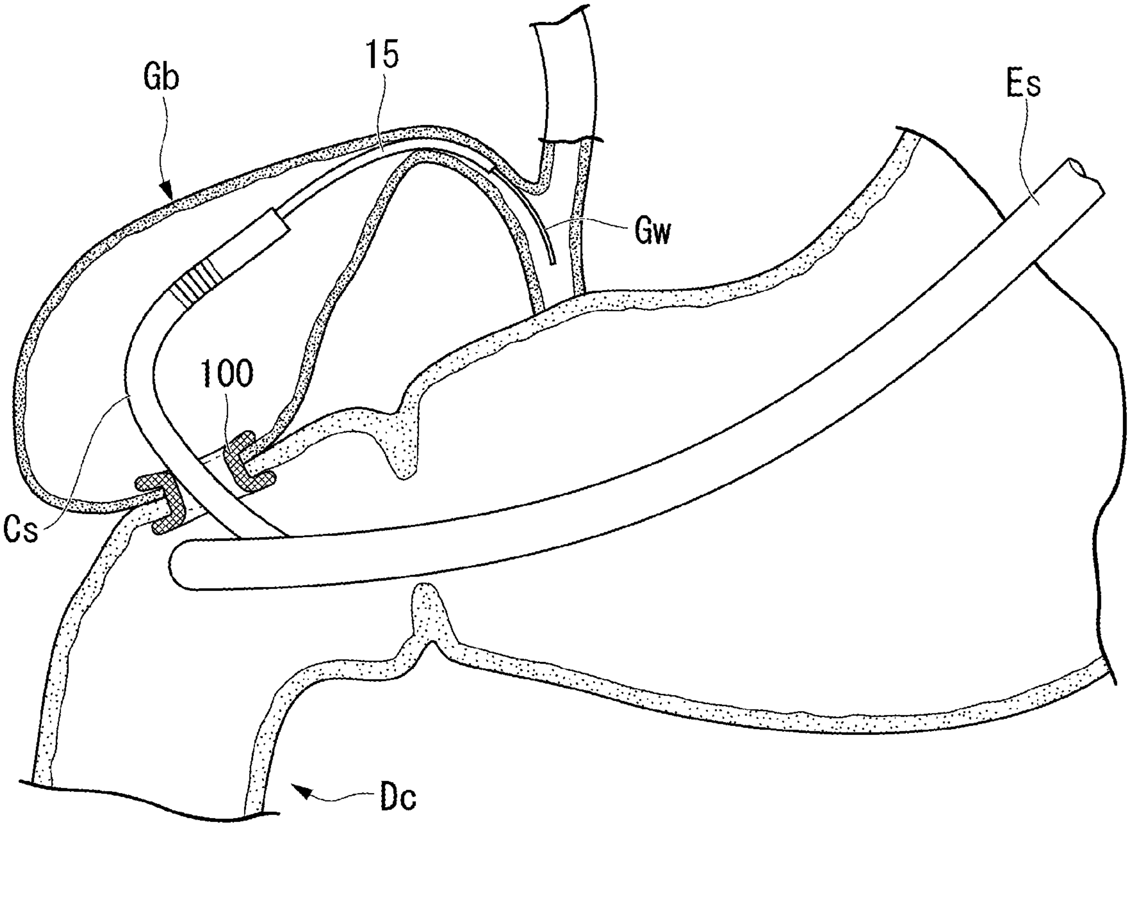
FIG. 4 is an illustration showing a portion of a process of step B according to a first embodiment of the present subject matter.

FIG. 4 shows an example of the procedure of step B when route B is selected. In FIG. 4, a bendable cholangioscope Cs is protruded from the treatment tool channel (e.g., "working channel") of the endoscope Es introduced into the duodenum Dc and inserted into the gallbladder Gb via opening defined by the stent 100. Further, the guide wire Gw is protruded from the treatment tool channel (e.g., "working channel") of the cholangioscope Cs and inserted into the cystic duct from the inside of the gallbladder Gb. The distal end of the inserted guide wire Gw can be positioned, for example, such as to be positioned in the common bile duct, the cystic duct, or out of the duodenal papilla through the common bile duct. The position of the distal end of the guide wire Gw can be confirmed by an X-ray fluoroscopic image or the like.

If route A is selected in step A, the gallbladder is punctured and the stent 100 is arranged in the same procedure as in step A of route B before step B.

Next, the delivery system of the bypass tube is inserted into the gallbladder tube using the guide wire Gw as a guide. The delivery system of the bypass tube can have a configuration similar, in some respects, to that of a bile duct stent delivery system, and in an example, has an introduction catheter or a delivery catheter or other tube guide, a bypass tube housed within the delivery catheter or other tube guide, and a pusher arranged behind the bypass tube or other tube guide within the delivery catheter. The pusher can help push the bypass tube 10 out of the catheter to a location such as with the first end located within and sealingly occluding the cystic duct. The tube guide is inserted into the cystic duct, the bypass tube 10 is carried by the tube guide, a first end of the bypass tube 10 is placed at the cystic duct, the tube guide is pulled to the connection area, and a second end of the bypass tube 10 is placed at the communication area.

Figure 5:
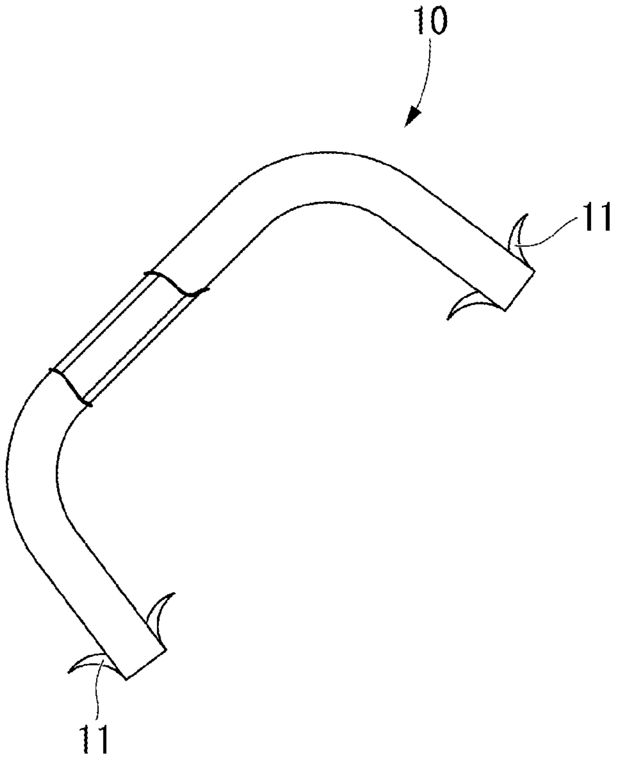
FIG. 5 is an illustration showing an example of a bypass tube.

FIG. 5 is a diagram showing an example of the bypass tube, such as which can be shaped or shapable to include one or more bends, such as to orient the ends of the bypass tube to their locations, such as explained herein. A bypass tube 10 is formed in a tubular shape such as by combining a synthetic resin, a metal wire, or the like. The bypass tube 10 has a length that is long enough to reach the duodenum from the cystic duct through the gallbladder of a typical or selected human subject. The bypass tube 10 can include one or more projections or other anchor or engagement members (anchoring engagement member) such as flaps 11 extending laterally or radially outward at both ends of the bypass tube 10. The bypass tube 10 has a first end having a first projection and a second end having a second projection. The first and second projections are arranged in a bile duct and duodenum respectively. The bypass tube 10 has flaps at both ends, one of the flaps is arranged in the cystic duct and the other of the flaps is arranged in the digestive tract. The first projection may be the first flap 11 extending in a radial direction of a first end of the bypass tube 10, and the second projection may be a second flap 11 extending in a radial direction of a second end of the bypass tube 10. The placing of the bypass tube 10 includes engaging a third projection 12 of the bypass tube 10, and the third projection 12 is located between the first projection 11 and the second projection 11. The engaging the first end includes one or more of sealing a space between the cystic duct and the bypass tube 10, suturing the cystic duct and attaching the first projection 11 of the bypass tube 10 to the cystic duct, and the engaging the second end includes one or more of sealing a space between the connection area and the bypass tube 10, suturing the connection area and attaching the second projection 11 of the bypass tube 10 to the connection area. The engaging the first end proceeds after the hooking or otherwise engaging a second end. The flaps 11 can be folded-in along the bypass tube 10 and housed in the delivery catheter during delivery. Then, when exiting the delivery catheter during deployment of the bypass tube 10 at a location, the flaps 11 can return outward from the folded-in delivery state, such as to the folded-out state in a radial direction of other lateral direction such as shown in FIG. 5, such as by their own elastic force of the flaps 11, such as for hooking or attaching or otherwise engaging or anchoring to tissue or another securement. The flaps 11 may include a resilient projecting flap that extends radially outward when the cholecystitis treatment device is deployed, and the resilient projecting flap folded-inward when the bypass tube 10 is located within a bypass tube introduction catheter 15. Additionally or alternatively to flaps 11, other examples of anchor or engagement members can include shape-memory or other resilient expandable stents, such as can include a self-expanding mesh or scaffolding upon release from delivery into the deployed position.

It is preferable that the shape of the bypass tube 10 match the route from the cystic duct to the duodenum, such as shown in FIG. 5, when it exits the delivery catheter and is deployed.

Figure 6:
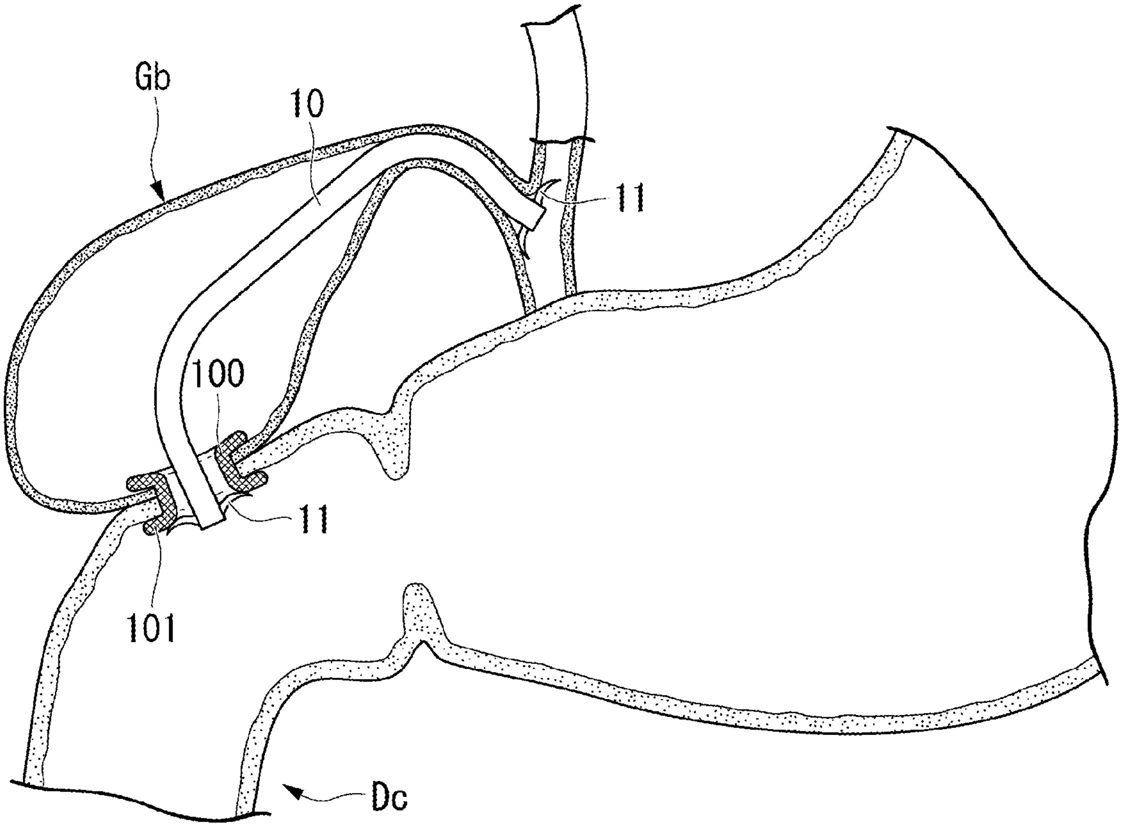
FIG. 6 is an example of an illustration showing a state in which an arrangement of the bypass tube is completed.

As shown in FIG. 4, the surgeon inserts a delivery catheter 15 (bypass tube introduction catheter) protruding from the cholangioscope Cs into the common bile duct via the gallbladder duct, and retracts the delivery catheter 15 while supporting the bypass tube 10 with a pusher. Then, the flaps 11 on the distal end side exit the delivery catheter and are deployed, and can be locked or anchored to the bifurcation between the common hepatic duct and the cystic duct. Then, the cholangioscope Cs and the delivery catheter are retracted, and the delivery catheter is gradually arranged in the gallbladder. When the cholangioscope Cs and the delivery catheter 15 are retracted into the duodenum, the entire bypass tube 10 moves out of the delivery catheter 15 and the arrangement of the bypass tube 10 is completed, as shown in FIG. 6. At the completion of placement, the distal end of the bypass tube 10 is located near the bifurcation between the common hepatic duct and the cystic duct. The posterior end of the bypass tube 10 is located in the duodenum and outside the stent 100, such as with the flap 11 on the posterior end side locked or anchored to the flange 101 of the stent 100. Hooking or attaching or otherwise engaging the first end of the bypass tube 10 can occur or proceed before the hooking or attaching or otherwise engaging the second end of the bypass tube 10, or vice-versa.

With the above, a series of procedures related to this embodiment is completed. In step B, the flap 11 or the bypass tube 10 itself may be sutured or sewn onto the stent 100 such as to help ensure that the posterior end is located within the duodenum. At such time, when the opening on the duodenum side of the stent 100 is narrowed such as using a suture thread or the like to make it smaller, and the gap with the outer peripheral surface of the bypass tube 10 is made smaller, the contents of the duodenum can be suppressed from entering the gallbladder.

By placing the bypass tube 10, the bile traveling from the common hepatic duct toward the cystic duct flows into and via the bypass tube 10 and is discharged into the duodenum. That is, the bypass tube 10 conveys bile that travels toward the cystic duct such that the bile does not contact the inner wall of the gallbladder and is not concentrated by the gallbladder. Therefore, the formation and growth of calculus do not occur, and the recurrence and relapse of cholecystitis are suitably suppressed.

After a lapse of time after indwelling, the bypass tube 10 may become narrowed or occluded by the bile component. However, because the space between the bypass tube 10 and the cystic duct is so narrow, most of the bile is drained from the duodenal papilla into the duodenum through the common bile duct. Therefore, in this case as well, bile does not come into contact with the inner wall of the gallbladder, the effect of suppressing recurrence and relapse of cholecystitis is maintained, and bile stasis does not occur.

As described above, the method of cholecystitis treatment according to the present embodiment can suitably suppress the recurrence or relapse of cholecystitis without removing the gallbladder. Therefore, the invasiveness to the patient can be significantly reduced, such as compared with laparoscopic cholecystectomy.

In step B, if the inner diameter of the stent 100 that communicates the gallbladder and duodenum is sufficiently large, an endoscope for the upper gastrointestinal tract may be inserted into the gallbladder without using the cholangioscope Cs, and the delivery system of the bypass tube 10 may be protruded from the endoscope and inserted into the gallbladder duct.

In an example, the bypass tube 10 may be directly inserted into the cystic duct and indwelled without placing the guide wire in advance.

Figure 7:
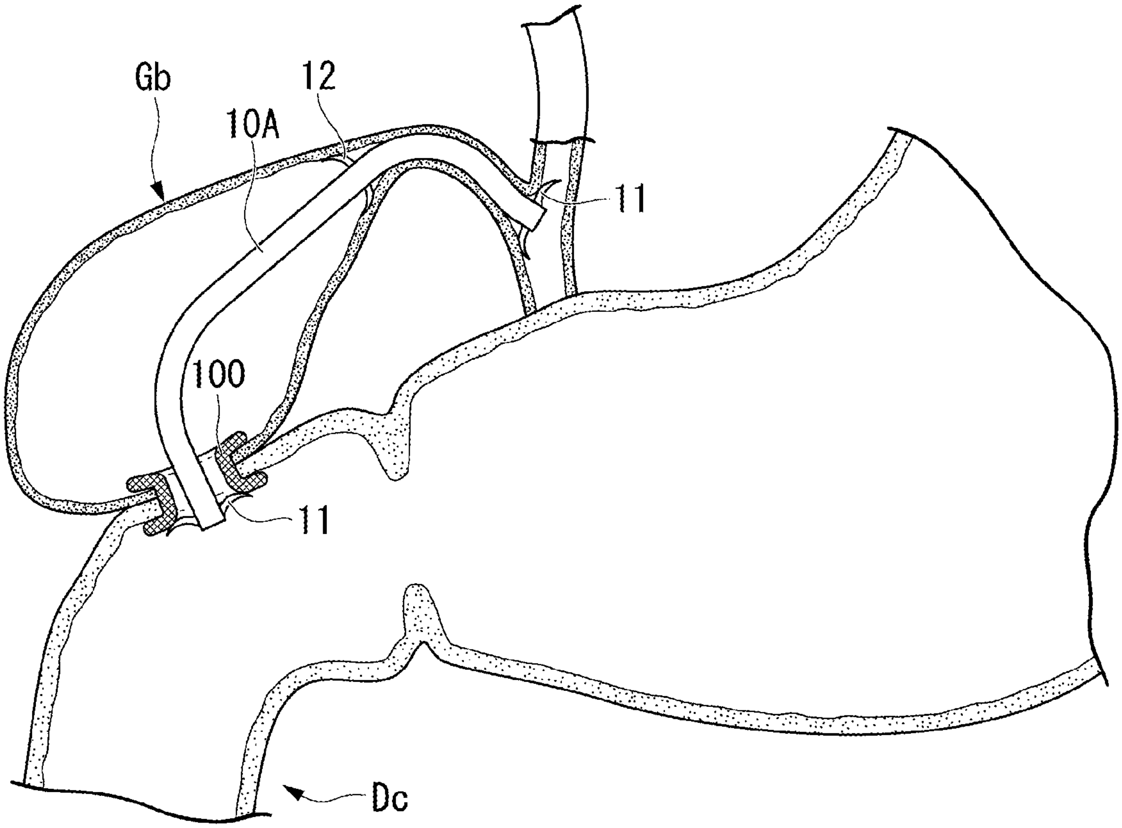
FIG. 7 is an illustration showing a state in which a bypass tube according to a modified example is indwelled.

The bypass tube 10 according to the present embodiment may have an auxiliary flap 12 (additional relatively more proximal anchoring engagement member) in the intermediate portion in the longitudinal direction or between the first end and the second end or a middle part of the bypass tube, the auxiliary flap 12 is arranged in the gallbladder Gb as in a bypass tube 10A shown in FIG. 7. The auxiliary flap 12 is arranged in the gallbladder. The auxiliary flap 12 from one of the first and second ends of the bypass tube. As shown in FIG. 7, by arranging and locking or anchoring or engaging the auxiliary flap 12 in the neck portion near the entrance of the gallbladder Gb, it is possible to more reliably inhibit or prevent the bypass tube from moving after arrangement.

The second embodiment of the present subject matter will be described with reference to FIGS. 8 and 9. In the following description, the same reference numerals will be given to the configurations and for brevity, similar explanation to what has already been described above will be omitted.

Figure 8:
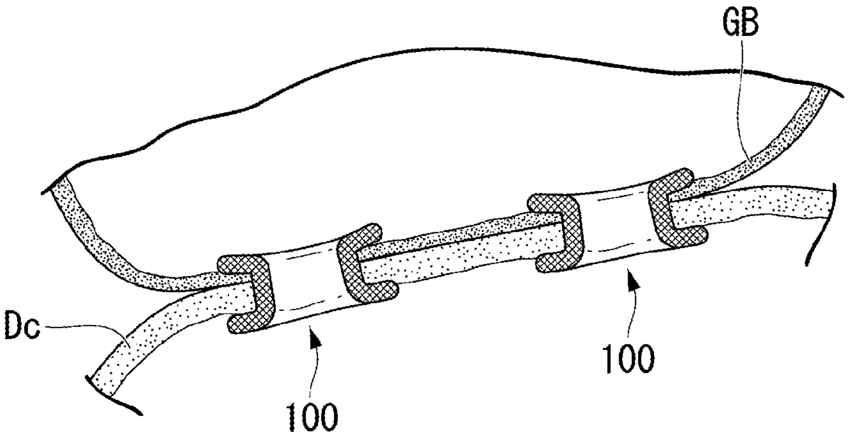
FIG. 8 is an illustration showing an examples of portions of a process of step A according to a second embodiment of the present subject matter.

First, step A is performed in the same manner as in the first embodiment, except that a plurality of stents 100 that communicate the gallbladder Gb and the duodenum Dc are arranged, such as shown in FIG. 8. After placement, it is confirmed or inspected by ultrasonic endoscopy or the like that the gallbladder Gb and the duodenum Dc are in sufficient contact with each other around each stent 100, and the procedure is temporarily completed.

By placing a plurality of stents 100, the gallbladder Gb and the duodenum Dc are maintained in close contact with each other in a wide area, and therefore this close contact state is maintained for about 2 weeks to 1 month (step C). In step C, the gallbladder and the duodenal tissue adhere to each other in a state in which the fistula is formed by stent arrangement, and the gallbladder Gb and the duodenal Dc adhere to each other around the fistula by tissue adhesions that form.

After step C, the surgeon can identify that the gallbladder Gb and the duodenum Dc are adhered by ultrasonic endoscopy or the like, and the position and area of the adhesion site. Then, an endoscope is inserted into the duodenum and a plurality of placed stents are removed. Further, an incision is made in the adhesion area with a high-frequency knife or the like to form a large hole or fistula communicating the gallbladder and the duodenum (step D).

Figure 9:
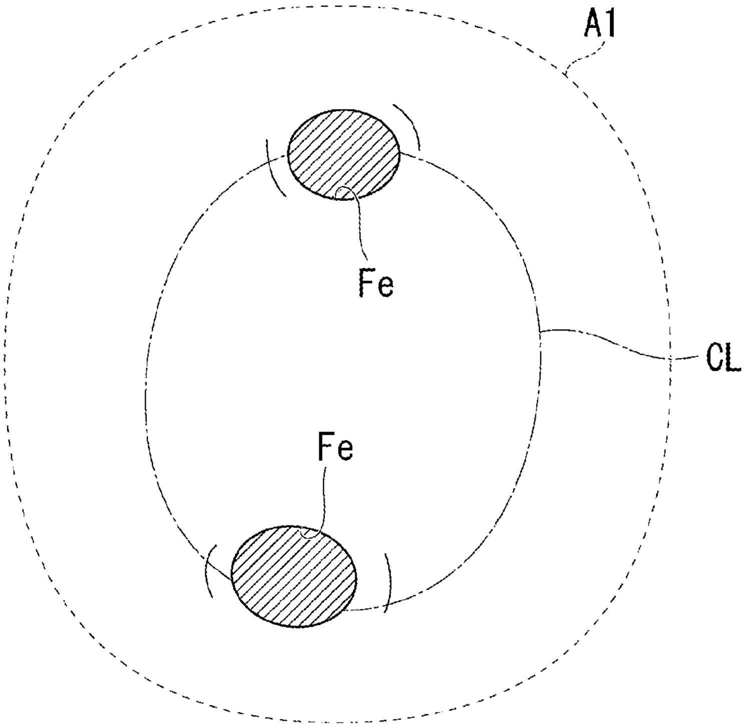
FIG. 9 is a view of an adhesion site between the gallbladder and the duodenum as viewed from the duodenum side.

FIG. 9 shows an example around the placing site of the stent as seen from the duodenum side. If the gallbladder and duodenum are adhered in a certain area A1 around the fistula Ft after removal of the stent, by incising the adhesion site along a cut line CL connecting the fistula Ft, a large hole communicating the gallbladder and the duodenum can be formed in the area A1. Marking or the like for grasping the cut line CL may be performed before the incision.

Finally, when the cystic duct is occluded (step E), a series of procedures according to the present embodiment is completed. For example, the cystic duct can be occluded by introducing an endoscope into the gallbladder through the hole formed in step D and performing cauterization, ligation with one or more clips or staples, adhesion, or the like.

Since the hole formed in step D is large, the contents of the duodenum containing gastric acid easily enter the gallbladder through the hole. As a result, the mucous membrane in the gallbladder is chemically altered by stomach acid and loses its ability to concentrate the bile. Although the gallbladder mucosa has the ability to repair, the contents frequently enter the gallbladder and continue to cause chemical alteration of the gallbladder mucosa, so that the state is maintained in which the function of concentrating the bile is reduced, and the recurrence and relapse of cholecystitis are preferably suppressed.

If such a condition continues for a long period of time, a phenomenon similar to intestinal metaplasia will occur in the gallbladder mucosa, causing mucosal degeneration, and it can be expected that cholecystitis will be completely cured by completely eliminating the function of concentrating the bile.

In the present embodiment, the means for maintaining close contact between the gallbladder and the duodenum is not limited to the stent described above. For example, a plurality of suture units including a thread, an anchor, and a stopper as described in US Patent Publication 2009/259232 may be used to maintain close contact between the gallbladder and the duodenum.

Although various embodiments of the present subject matter has been described above, the technical scope of the present subject matter is not limited to the above embodiments. It is possible to change the combination of components, make various changes to each component, and delete them without departing from the present disclosure. In addition to the changes described above, some additional changes are exemplified, but these are not all, and other changes are possible. Two or more of these changes may be combined as appropriate, or may be combined with the changes described above.

In the treatment method according to the present subject matter, it is not essential to clean the inside of the gallbladder. However, by thoroughly cleaning the inside of the gallbladder after physical or chemical treatment, the remaining tissue, bile, and drugs or other chemicals can be sufficiently discharged, so that the gallbladder can be in close contact in a clean state. Adhering the gallbladder has the advantage of helping inhibiting or preventing cholecystitis due to residual bile.

Although it is slightly different from the treatment method according to the present subject matter, the therapeutic effect on cholecystitis can be obtained even if step B of the first embodiment is changed as follows.

Figure 10:
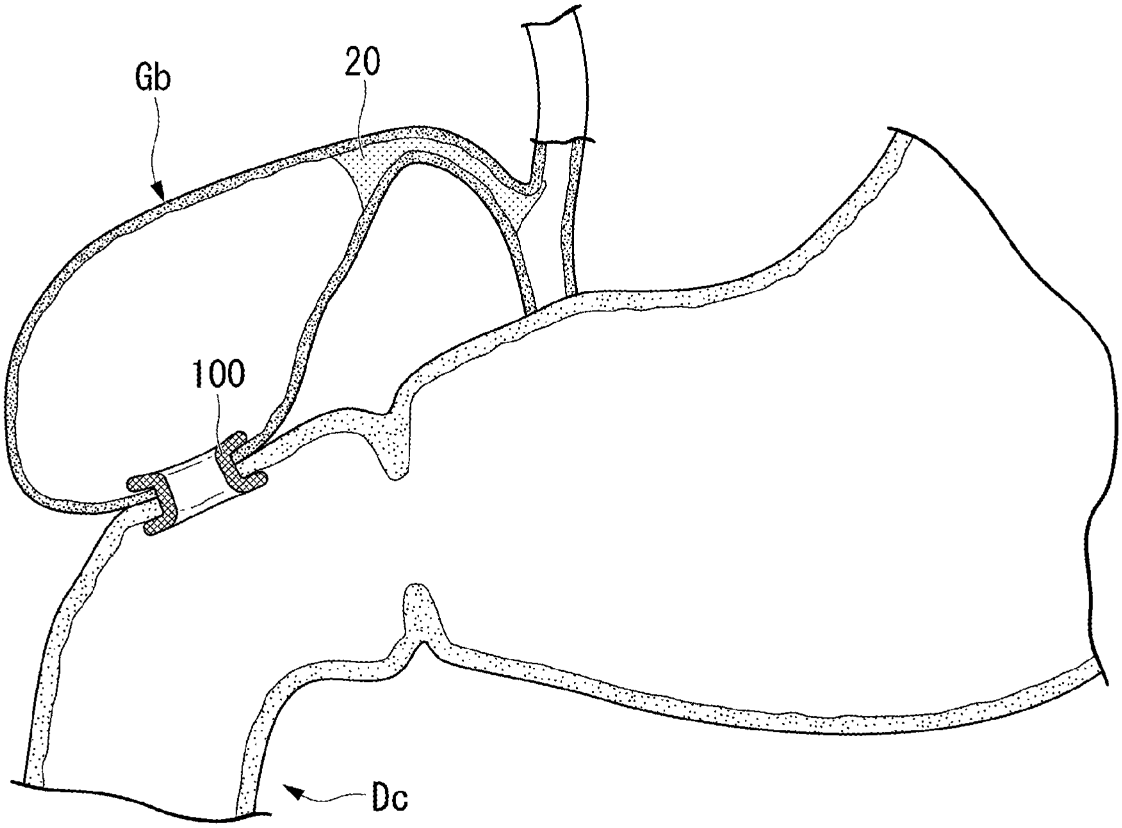
FIG. 10 is an illustration showing another example of portions of step B.

A solid plug 20 as shown in FIG. 10 is arranged in the cystic duct to help inhibit or prevent bile from flowing into the gallbladder. The plug 20 has a large diameter at both ends, and by interfering with the gallbladder and the bile duct at both ends, the plug 20 can maintain the indwelled state without coming out of the cystic duct.

By obstructing the cystic duct, the inflow of bile into the gallbladder is suppressed. Closure of the cystic duct can be performed in the same procedure as in step E of the second embodiment. Furthermore, while checking the cystic duct under endoscopic ultrasound, the cystic duct can be occluded by injecting an adhesive by protruding a puncture needle from an endoscope arranged in the duodenum to puncture the cystic duct.

In the treatment method according to the present subject matter, it is not essential to arrange a stent in the port, fistula, or other communication hole. For example, the communication hole formed by puncture may be temporarily expanded with a balloon or the like, and the communication hole may be sewn after passing through the bypass tube to eliminate the gap with the bypass tube.

Example 1. A method of cholecystitis treatment, the method comprising:

- forming a fluid communication hole that communicates a gallbladder and a duodenum; and
- arranging a bypass tube extending from a cystic duct to the duodenum through the inside of the gallbladder and the communication hole.

Example 2. The method of cholecystitis treatment according to Example 1, wherein the bypass tube is first arranged in the gallbladder and then arranged in the duodenum by a device that has entered the gallbladder.

Example 3. The method of cholecystitis treatment according to Example 1, wherein the bypass tube has flaps or other engagement members at both ends, and

- wherein one of the flaps is arranged in the bile duct and the other of the flaps is arranged in the duodenum.

Example 4. The method of cholecystitis treatment according to Example 3, wherein the bypass tube has an auxiliary flap in a middle part, and

- the auxiliary flap is arranged in the gallbladder.

Example 5. The method of cholecystitis treatment according to Example 1, wherein the communication hole is formed by puncturing the gallbladder from within the duodenum.

Example 6. The method of cholecystitis treatment according to Example 1, wherein a stent is arranged in the communication hole.

Example 7. A method of cholecystitis treatment, the method comprising:

- forming a first hole on a gallbladder and a second hole on a digestive tract;
- connecting the first hole and the second hole to form a fistula or other connection area; and
- placing a bypass tube connecting the connection area to a cystic duct.

Example 8. The method of cholecystitis treatment according to Example 7, wherein the placing includes hooking or otherwise engaging a first projection of the bypass tube.

Example 9. The method of cholecystitis treatment according to Example 7, wherein the first projection is at a first end of the bypass tube.

Example 10. The method of cholecystitis treatment according to any of Examples 7 through 8, wherein the first projection has a flap or other engagement member extending in a radial or other lateral direction of the bypass tube.

Example 11. The method of cholecystitis treatment according to any of Examples 7 through 10, wherein the placing includes hooking or otherwise engaging a first projection of the bypass tube on the cystic duct and hooking or otherwise engaging a second projection of the bypass tube on the connection area.

Example 12. The method of cholecystitis treatment according to any of Examples 8 through 11, wherein the first projection is at a first end of the bypass tube, and wherein the second projection is at a second end of the bypass tube.

Example 13. The method of cholecystitis treatment according to any of Examples 8 through 12, wherein the first projection has a first flap extending in a radial or other lateral direction of the bypass tube, and wherein the second projection has a second flap extending in a radial or other lateral direction of the bypass tube.

Example 14. The method of cholecystitis treatment according to any of Examples 7 through 13, wherein the placing includes hooking or otherwise engaging a third projection of the bypass tube, and wherein a third projection is located between the first projection and the second projection.

Example 15. The method of cholecystitis treatment according to any of Examples 7 through 14, wherein the bypass tube has a first end and a second end, wherein the placing includes hooking or otherwise engaging the first end at the cystic duct and hooking or otherwise engaging the second end at the connection area.

Example 16. The method of cholecystitis treatment according to Example 15, wherein the hooking or otherwise engaging the first end includes one or more of sealing a space between the cystic duct and the bypass tube, suturing the cystic duct and attaching a first projection of the bypass tube to the cystic duct, and wherein the hooking the second end includes one or more of sealing a space between the connection area and the bypass tube, suturing the connection area and attaching a second projection of the bypass tube to the connection area.

Example 17. The method of cholecystitis treatment according to any of Examples 15 through 16, wherein the hooking or otherwise engaging the second end proceeds after the hooking or otherwise engaging the first end.

Example 18. The method of cholecystitis treatment according to Example 11, wherein the hooking or otherwise engaging the first end proceeds after the hooking or otherwise engaging a second end.

Example 19. The method of cholecystitis treatment according to any of Examples 7 through 18, wherein the bypass tube is sized, shaped, or otherwise configured to inhibit or prevent movement into the gallbladder after placement of the bypass tube.

Example 20. The method of cholecystitis treatment according to any of Examples 7 through 19, wherein the forming includes puncturing the gallbladder from a side of the cystic duct.

Example 21. The method of cholecystitis treatment according to any of Examples 7 through 20, wherein the forming includes puncturing the cystic duct from a side of the gallbladder.

Example 22. The method of cholecystitis treatment according to any of Examples 7 through 21, wherein the connecting includes placing a stent or other port at the connection area.

Example 23. The method of cholecystitis treatment according to any of Examples 7 through 22, wherein the connecting includes suturing the gallbladder and digestive tract.

Example 24. The method of cholecystitis treatment according to any of Examples 7 through 23, wherein the connecting includes sealing the gallbladder and digestive tract.

Example 25. The method of cholecystitis treatment according to any of Examples 7 through 24, wherein the placing includes inserting a tube guide to the cystic duct, and wherein the placing includes inserting the bypass tube into the tube guide.

Example 26. The method of cholecystitis treatment according to any of Examples 7 through 25, wherein the placing includes:

inserting a tube guide to the cystic duct,
inserting the bypass tube carried by the tube guide,
placing a first end of the bypass tube at the cystic duct,
pulling the tube guide to the connection area, and
placing a second end of the bypass tube at the connection area.

Example 27. A cholecystitis treatment device for conveying bile fluids from a cystic duct to a fistula between a gallbladder and a digestive tract in a human subject, the cholecystitis treatment device comprising:

a bypass tube, including first and second ends and bypass tube body extending therebetween, the bypass tube body defining a fluid communication lumen between the first and second ends for communicating bile fluids therebetween, the first end sized and shaped to extend to and conform within the cystic duct, the second end sized and shaped to extend to, within, or beyond a fistula between the gallbladder and a portion of the digestive tract, a length of the bypass tube body sized to extend from the first end to the second end within the gallbladder of the subject.

Example 28. The cholecystitis treatment device of Example 27, comprising an anchoring engagement member located at at least one of the first or second ends of the bypass tube.

Example 29. The cholecystitis treatment device of Example 28, wherein the anchoring engagement member includes a projecting flap that extends radially or otherwise laterally outward when the cholecystitis treatment device is deployed.

Example 30. The cholecystitis treatment device of any of Examples 10, 13, and 29, wherein the projecting flap is a resilient projecting flap that is folded-inward when the bypass tube is located within a bypass tube introduction catheter or other tube guide.

Example 31. The cholecystitis treatment device of any of Examples 27 through 30, further comprising the bypass tube introduction catheter and a pusher arranged to push the bypass tube out of the bypass tube introduction catheter or other tube guide.

Example 32. The cholecystitis treatment device of any of Examples 27 through 31, further comprising a guidewire arranged to deploy at least one of the bypass tube, the bypass tube introduction catheter, or the bypass tube guide over the guidewire.

Example 33. The cholecystitis treatment device of any of Examples 27 through 32, further comprising an additional relatively more proximal anchoring engagement member from at least one of the first or second ends of the bypass tube.

Example 34. The cholecystitis treatment device of any of Examples 27 through 33, wherein the bypass tube is sized and shaped to be delivered to the fistula via a working channel of a duodenoscope or other endoscope that is sized and shaped and otherwise configured to be introduced endoscopically and through a duodenum to or beyond the fistula, wherein the fistula is between the duodenum and a portion of the gallbladder located proximal to the duodenum and distal from the cystic duct.

Example 35. The cholecystitis treatment device of any of Examples 27 through 34, further comprising the duodenoscope or other endoscope.

Example 36. The cholecystitis treatment device of any of Examples 27 through 35, further comprising a stent or other port device configured to be located at the fistula and to secure the gallbladder to a duodenum.

Example 37. The cholecystitis treatment device of Example 36, wherein the stent or other port device includes one or more flanges to secure at least one of a wall of the gallbladder or a wall of the duodenum with respect to the stent or other port device.

Example 38. The cholecystitis treatment device of any of Examples 35 through 37, wherein the stent or other port device includes one or more suture receptacles for suturing the stent or other port device to at least one of a wall of the gallbladder or a wall of the duodenum.

Example 39. The cholecystitis treatment device of any of Examples 27 through 38, wherein the bypass tube is shaped or shapable with one or more bends such that when the bypass tube is deployed within the gallbladder, the first end is orientable toward the cystic duct while the second end is orientable toward the fistula, and wherein the fistula is between a portion of the gallbladder that is distal from the cystic duct and a portion of the digestive tract that includes a duodenum.

Example 40. A cholecystitis treatment device for a gallbladder of a human subject, the cholecystitis treatment device comprising:

a stent or other port device configured to be located at a fistula between the gallbladder and a portion of a digestive tract of the subject; and a plug, sized and shaped and otherwise configured to be located within and to sealingly occlude a cystic duct associated with the gallbladder.

Example 41. The cholecystitis treatment device of Example 40, wherein the stent or other port device includes one or more flanges to secure at least one of a wall of the gallbladder or a wall of a duodenum with respect to the stent or other port device.

Example 42. The cholecystitis treatment device of any of Examples 40 through 41, wherein the stent or other port device includes one or more suture receptacles for suturing the stent or other port device to at least one of a wall of the gallbladder or a wall of the duodenum.

Example 43. A method of cholecystitis treatment, the method comprising:

occluding a cystic duct via a first end of a bypass tube;

providing a fluid communication lumen from the first end of the bypass tube to a second end of the bypass tube located at a fistula between a gallbladder and a portion of a digestive tract; and conveying bile fluids from the first end of the bypass tube to the second end of the bypass tube via the fluid communication lumen of the bypass tube.

Example 44. A medical method as shown and described herein.

Example 45. A medical device as shown and described herein.

What is claimed is:

1. A method of cholecystitis treatment, the method comprising:

forming a fluid communication hole that communicates a gallbladder and a digestive tract; and arranging a bypass tube extending from a cystic duct to the digestive tract through an inside of the gallbladder and the fluid communication hole.

2. The method of cholecystitis treatment according to claim 1, wherein the bypass tube is first arranged in the gallbladder and then arranged in the digestive tract by a device that has entered the gallbladder.

3. The method of cholecystitis treatment according to claim 1, wherein the bypass tube has flaps at both ends, and one of the flaps is arranged in the bile duct and the other of the flaps is arranged in the digestive tract.

4. The method of cholecystitis treatment according to claim 3, wherein the bypass tube has an auxiliary flap in a middle part, and the auxiliary flap is arranged in the gallbladder.

5. The method of cholecystitis treatment according to claim 1, wherein the fluid communication hole is formed by puncturing the gallbladder from within the digestive tract.

6. The method of cholecystitis treatment according to claim 1, wherein a stent is arranged in the fluid communication hole.

7. The method of cholecystitis treatment according to claim 1, the method comprising:

forming a first hole on the gallbladder and a second hole on the digestive tract;

connecting the first hole and the second hole to form a connection area; and wherein the arranging includes placing the bypass tube connecting the connection area to the cystic duct.

8. The method of cholecystitis treatment according to claim 7, wherein the placing includes engaging a first projection of the bypass tube on the cystic duct.

9. The method of cholecystitis treatment according to claim 8, wherein the placing includes engaging a second projection of the bypass tube on the connection area.

10. The method of cholecystitis treatment according to claim 9, wherein the connecting includes one of placing a stent at the connection area, suturing the gallbladder and digestive tract, and sealing the gallbladder and digestive tract.

11. The method of cholecystitis treatment according to claim 9, wherein the first projection has a first flap extending in a radial direction of a first end of the bypass tube, and the second projection has a second flap extending in a radial direction of a second end of the bypass tube.

12. The method of cholecystitis treatment according to claim 11, wherein the placing includes engaging a third projection of the bypass tube, and the third projection is located between the first projection and the second projection.

13. The method of cholecystitis treatment according to claim 11, wherein the engaging the first end includes one or more of sealing a space between the cystic duct and the bypass tube, suturing the cystic duct and attaching a first projection of the bypass tube to the cystic duct, and the engaging the second end includes one or more of sealing a space between the connection area and the bypass tube, suturing the connection area and attaching a second projection of the bypass tube to the connection area.

14. The method of cholecystitis treatment according to claim 11, wherein engaging the first end proceeds after the hooking or otherwise engaging a second end.

15. The method of cholecystitis treatment according to claim 7, wherein the forming includes puncturing one of (i) the gallbladder from a side of the cystic duct and (ii) the gallbladder from a side of the digestive tract.

16. The method of cholecystitis treatment according to claim 7, wherein the placing includes:

inserting a tube guide to the cystic duct, inserting the bypass tube carried by the tube guide, placing a first end of the bypass tube at the cystic duct, pulling the tube guide to the connection area, and placing a second end of the bypass tube at the connection area.

* * * * *